United States Patent
Dernbach et al.

(12) 
(10) Patent No.: US 6,809,224 B2
(45) Date of Patent: Oct. 26, 2004

(54) METHOD FOR THE SEPARATION OF FORMALDEHYDE FROM A REACTION MIXTURE CONTAINING POLYOLS BY THE ADDITION OF SOLVENTS BEFORE AND/OR DURING THE DISTILLATION

(75) Inventors: Matthias Dernbach, Dossenheim (DE); Detlef Kratz, Heidelberg (DE); Achim Stammer, Freinsheim (DE); Gerhard Schulz, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/168,999

(22) PCT Filed: Dec. 27, 2000

(86) PCT No.: PCT/EP00/13293

§ 371 (c)(1),
(2), (4) Date: Jun. 26, 2002

(87) PCT Pub. No.: WO01/47854

PCT Pub. Date: Jul. 5, 2001

(65) Prior Publication Data

US 2003/0023119 A1 Jan. 30, 2003

(30) Foreign Application Priority Data

Dec. 28, 1999 (DE) .......................................... 199 63 445

(51) Int. Cl.⁷ ............................................... C07C 45/82
(52) U.S. Cl. ........................ 568/493; 568/458; 568/492; 568/853; 568/862; 568/863

(58) Field of Search ................................. 568/458, 492, 568/493, 853, 862, 863

(56) References Cited

U.S. PATENT DOCUMENTS

| | | | |
|---|---|---|---|
| 4,036,888 A | | 7/1977 | Couderc ...................... 260/602 |
| 4,594,461 A | * | 6/1986 | Merger et al. ............... 568/853 |
| 5,177,267 A | * | 1/1993 | Morris et al. ................ 568/492 |
| 5,235,118 A | | 8/1993 | Morris ......................... 568/862 |
| 6,018,074 A | * | 1/2000 | Kratz et al. .................. 560/234 |

FOREIGN PATENT DOCUMENTS

| | | | |
|---|---|---|---|
| SU | 273 434 | 11/1989 | ........... C07C/29/80 |
| WO | WO 96/19635 | 6/1996 | |

OTHER PUBLICATIONS

Am. Chm.Soc. JP 10287606—129:275637

* cited by examiner

*Primary Examiner*—Rosalynd Keys
(74) *Attorney, Agent, or Firm*—Keil & Weinkauf

(57) ABSTRACT

Formaldehyde is removed by distillation from reaction solutions containing a methlolated alkanal which was obtained from the reaction of formaldehyde with an alkanal which has at least one acidic hydrogen atom α to the carbonyl function or from the reaction of a 2-alkylacrolein or acrolein with water and formaldehyde, by a process in which this reaction was carried out in the presence of catalytic amounts of organic amine. The process permits the improved removal of formaldehyde from the reaction mixture and furthermore facilitates the hydrogenation of the alkanals thus obtained to give polyols.

22 Claims, No Drawings

METHOD FOR THE SEPARATION OF FORMALDEHYDE FROM A REACTION MIXTURE CONTAINING POLYOLS BY THE ADDITION OF SOLVENTS BEFORE AND/OR DURING THE DISTILLATION

The present invention relates to the area of industrial organic chemistry. More precisely, the present invention relates to a process for effectively removing formaldehyde from methylolalkanal solutions. The present invention furthermore relates to a process for hydrogenating methylolalkanals thus obtained to give polyols.

The condensation of formaldehyde with CH-acidic higher alkanals to give methylolalkanals, in general dimethylol- and trimethylolalkanals, and conversion of the compounds obtained to polyols constitute a widely used process in chemistry. Examples of important triols obtained in this manner are trimethylolpropane, trimethylolethane and trimethylolbutane, which are widely used for the production of finishes, urethanes and polyesters. Other important compounds are pentaerythritol, obtainable by condensation of formaldehyde and acetaldehyde, and neopentylglycol from isobutyraldehyde and formaldehyde. The tetrahydric alcohol pentaerythritol is also frequently used in the coatings industry but is also very important in the production of explosives.

The polyols can be prepared by various processes. One method is the Cannizzaro process, which is further subdivided into the inorganic and the organic Cannizzaro process. In the inorganic variant, an excess of formaldehyde is reacted with the corresponding alkanal in the presence of stoichiometric amounts of an inorganic base, such as NaOH or $Ca(OH)_2$. The methylolalkanal formed in the first stage reacts in the second stage with the excess formaldehyde in a disproportionation reaction to give the corresponding polyol and the formate of the corresponding base, i.e. for example sodium formate or calcium formate. The production of these salts is a disadvantage since they are difficult to separate from the reaction product and moreover one equivalent of formaldehyde is lost.

In the organic Cannizzaro process, a tertiary alkylarnine is used instead of an inorganic base. Consequently, higher yields can be achieved than with an inorganic base. Trialkylanmonium formate is obtained as an undesirable byproduct. Thus, here too, one equivalent of formaldehyde is lost.

The disadvantages of the Cannizzaro process are avoided in the hydrogenation process. Here, formaldehyde is reacted with the corresponding alkanal in the presence of catalytic amounts of an amine. Consequently, the reaction stops at the methylolalkanal stage. After removal of the formaldehyde, the reaction mixture, which still contains small amounts of the corresponding triol in addition to the corresponding alkanal, is subjected to a hydrogenation in which the desired polyol is obtained.

Different variants of these hydrogenation processes are described, inter alia, in the applications DE-A-25 07 461, DE-A-27 02 582, DE-A-27 14 516, DE-A-28 13 201, DE-A-33 40 791 and WO 98/28253.

A major problem of the hydrogenation process is effective removal of the formaldehyde used in excess, after the condensation reaction, before the use of the reaction mixture in the hydrogenation. Effective removal of the formaldehyde is desirable simply because it can be recycled to the reaction and is thus not lost. In principle, it would be possible to hydrogenate the reaction mixture directly after the condensation without prior removal of the formaldehyde. However, this would be converted into the relatively useless methanol; furthermore, an increased consumption of hydrogen and a higher catalyst loading would also be the result, so that an unfavorable balance would be obtained in the end.

The literature describes various methods for effectively separating formaldehyde from the reaction mixtures of the condensation. In connection with the present invention, the references cited below are of interest.

DD-A-273 434 describes a process for separating excess formaldehyde from reaction solutions, in which formaldehyde is reacted with its higher alkanals by the classical Cannizzaro process. A crude mixture containing the polyhydric alcohol and the formaldehyde used in excess is obtained. Formaldehyde is separated by addition of methanol, water and/or acetonitrile and subsequent azeotropic distillation of the formaldehyde as a complex mixture with the added solvents and further components. The polyhydric alcohol remains in the bottom.

Japanese Patent JP 10287606 (cited according to CA 1998/129: 275637) describes a process for removing formaldehyde from reaction mixtures which originate from the reaction of this aldehyde with higher aldehydes and contain the corresponding dimethylolalkanal as a product. The removal is effected by distillation in a thin-film evaporator. Before the distillation, water is added to the mixture, in amounts of >4 parts by weight. As a result of the distillation, a residual formaldehyde content of 5% is reached, at pressures of from 0.5 to 1 bar.

U.S. Pat. No. 4,036,888 also describes the addition of water to reaction mixtures of the reaction of formaldehyde with higher aldehydes and subsequent distillation. In this case, isobutyraldehyde is used and the product is hydroxypivalaldehyde. By adding water, the isobutyraldehyde used in excess is effectively removed here. For this reason, the problem of removing formaldehyde does not exist here since it is present after the reaction only in very small amounts.

The same also applies to U.S. Pat. No. 5,235,118, which relates to the reaction of 2-ethylhexanal with formaldehyde to give 2-ethyl-2-(hydroxymethyl)hexanal. Here too, formaldehyde is used in substoichiometric amounts relative to the 2-ethylhexanal, and only a small residue of formaldehyde is present in the product solution. The addition of water with subsequent distillation serves for effective removal of unreacted 2-ethylhexanal.

It is an object of the present invention to provide a process which permits effective removal of formaldehyde from the methylolalkanals obtained after reaction of formaldehyde with higher aldehydes. The separation should be so effective that the subsequent hydrogenation of the methylolalkanal is economical.

We have found that this object is achieved by a process for the removal, by distillation, of formaldehyde from reaction solutions containing a methylolated alkanal which was obtained from the reaction of formaldehyde with an alkanal which has at least one acidic hydrogen atom ax to the carbonyl function or from the reaction of a 2-alkylacrolein or acrolein with water and formaldehyde, this reaction having been carried out in the presence of catalytic amounts of an organic amine, wherein a suitable amount of water is added before and/or during distillation.

We have found that this object is furthermore achieved by a process for the preparation of polyols, wherein a methylolated alkanal which was freed from formaldehyde according to the process described above is subjected to a hydrogenation known per se.

It was found that effective separation can be achieved by adding water before and/or during the removal of formaldehyde by distillation from the methylolalkanal obtained after the condensation of formaldehyde with a higher aldehyde. Furthermore, the yield in a subsequent hydrogenation can be increased by adding water.

In general, the methylolalkanals will be di- or trimethylolalkanals. The methylolalkanals are generally prepared by condensation of the abovementioned starting compounds in the presence of catalytic amounts of an organic amine. In the present process, it is possible in general to use virtually all formaldehyde-containing discharges from an aldol condensation which are prepared by said condensation reaction. The process can be particularly advantageously used in the case of discharges from an aldol condensation which were obtained according to WO 98/28253. The content of this application is hereby incorporated by reference in the present application.

The removal of the formaldehyde from the aldol condensation mixtures is effected in a suitable distillation apparatus. Such apparatuses are known to those skilled in the art. It is preferable to use a distillation column.

Suitable distillation columns have from 3 to 100 theoretical plates. The best results were obtained with from 5 to 60 theoretical plates. These theoretical plates can be achieved by the usual measures. Trays, stacked packings and dumped packings may be mentioned here as non-restricting examples. These theoretical plates are preferably designed in such a way that residence times of from 1 to 300, particularly preferably from 10 to 180, minutes are achieved.

The column is operated in the distillation at from 50 to 160° C. The chosen pressure is from 20 mbar to 5 bar, preferably from 1 to 3 bar, in particular from 1.5 to 3 bar. The column is adjusted in such a way that a reflux ratio of from 100 to 0, preferably from 3 to 0, results. The reaction mixture to be separated is preferably fed in in the upper half of the column or at the top of the column.

To permit effective removal of the formaldehyde, water is fed in at a suitable point of the column. Water can be added in the form of liquid water or, preferably, in the form of steam. The feed can be effected at various points in the distillation column or the bottom, a feed with the feed stream or below it being preferred. A feed into the bottom of the column or into the evaporator is particularly preferred. The water is metered in such a way that its amount is from 0.1 to 10 parts of the feed stream. Owing to the temperature sensitivity of the product mixture, it is preferred in connection with the present invention to operate the column with an evaporator which has a low wall temperature and a small liquid content. It has proven particularly advantageous to employ a falling-film evaporator.

In a preferred embodiment of the present invention, the bottom of the column and the bottom of the evaporator are designed in such a way that the residence time of the bottom discharge, i.e. of the methylolated alkanal, from which formaldehyde has been removed, in water is from 1 to 300 minutes. Particularly preferred residence times are from 5 to 120 minutes. In the case of these residence times chosen in this manner, an optimum is achieved with regard to removal of formaldehyde and avoidance of the formation of undesirable byproducts.

The product stream which is obtained after the purification and consists of a mixture of the methylolated alkanal with water is generally removed from the bottom of the column or, if the distillation apparatus has a divided bottom, from the evaporator circulation stream obtained downstream of the evaporator or from the bottom of the evaporator.

Owing to the broad condensation curve of the vapor emerging at the top of the column, it is advantageous to use a condenser with liquid recycling. The direct condensation in a quench with cooled liquid circulation is particularly advantageous.

The novel process can be used for removing formaldehyde from all mixtures which result from its reaction with alkanals or its reaction with water and acrolein or 2-alkylacrolein. Examples of aldehydes are aliphatic aldehydes of 2 to 24 carbon atoms which may have a linear or branched chain or may contain alicyclic groups. All that is required is that at least one acidic hydrogen atom is present a to the carbonyl function. This also applies to aralkylaldehydes, which may be used as starting material. In general, those aldehydes of 8 to 24, preferably 8 to 12, carbon atoms are used. Examples of suitable aldehydes are 3-ethyl-, 3-n-propyl-, 3-isopropyl-, 3-n-butyl-, 3-isobutyl-, 3-sec-butyl- and 3-tert-butylbutanal and corresponding n-pentanals, n-hexanals and n-hepthnals; 4ethyl-, 4-n-propyl-, 4-isopropyl-, 4-n-butyl-, 4-isobutyl-, 4-sec-butyl- and 4-tert-butylpentanals, -n-hexanals and -n-heptanals; 5-ethyl-, 5-n-propyl-, 5-isopropyl-, 5-n-butyl-, 5-isobutyl-, 5-sec-butyl- and 5-tert-butyl-n-hexanals and -n-heptanals; 3-methylhexanal, 3-methylheptanal; 4-methylpentanal, 4-methylheptanal, 5-methylhexanal, 5-methylheptanal; 3,3, 5-trimethyl-n-pentyl-, 3,3-diethylpentyl-, 4,4-diethylpentyl-, 3,3-dimethyl-n-butyl-, 3,3-dimethyl-n-pentyl-, 5,5-dimethyl-heptyl-, 3,3-dimethylheptyl-, 3,3,4-trimethylpentyl-, 3,4-dimethylheptyl-, 3,5-dimethylheptyl-, 4,4-dimethylheptyl-, 3,3-diethylhexyl-, 4,4-dimethylhexyl-, 4,5-dimethylhexyl-, 3,4-dimethylhexyl-, 3,5-dimethythexyl-, 3,3-dimethylhexyl-, 3,4-diethylhexyl-, 3dimethyl4-ethylpentyl-, 3-methyl-4-ethylhexyl-, 3,3,4-trimethylpentyl-, 3,4,4-trinethylpentyl-, 3,3,4-trimethylhexyl-, 3,4,4-trimethylhexyl- and 3,3,4,4-tetramethylpentylaldehyde; in particular C2- to C12-n-alkanals.

Examples of alkylacroleins are methacrolein, 2-ethylacrolein, 2-propylacrolein and 2-hydroxymethylacrolein.

Particularly preferably used starting compounds are acetaldehyde for the preparation of pentaerytritol, propionaldehyde for the preparation of trimethylolethane, n-butyraldehyde for the preparation of TMP, n-pentanal for the preparation of trimethylolbutane and isobutyraldehyde for the preparation of neopentylglycol.

The purified product stream is then subjected to a hydrogenation in order to convert the alkanal function into an alcohol function and thus to prepare polyalcohols, in general triols or tetrahydric alcohols or diols. It was found that the product mixtures which result from the process according to the present invention and have a higher water content than the product mixtures described to date give particularly advantageous results in the hydrogenation. It was surprisingly found that the higher water content is not disadvantageous but the opposite. For example, it was found that, as a result of the increased dilution, the subsequent hydrogenation is substantially more selective with respect to the alkanal. Furthermore, the increased dilution also has an advantageous effect on the life of the catalyst, which is deactivated substantially more slowly.

The present invention furthermore relates to a process for the hydrogenation of methylolalkanals which were obtained by the process according to the present invention and have a higher water content.

Hydrogenation is carried out under the conditions known in the literature and using the known materials. Copper-containing catalysts are preferably used. Further preferred catalysts are described in the applications DE-A-24 45 303, DE-A-198 09 418, DE-A-197 30 939 and WO 95/32171. The hydrogenations are carried out at from 5 to 250, preferably from 10 to 200, particularly preferably from 20 to 150, bar.

The examples which follow illustrate the invention. In these examples, the aldol condensation mixture used had been prepared as follows:

An apparatus consisting of two heatable stirred kettles connected to one another by overflow pipes and having a total capacity of 72 l was continuously fed with fresh, aqueous formaldehyde solution (4300 g/h) in the form of a 40% strength aqueous solution or n-butyraldehyde (1800 g/h) and with fresh trimethylamine as catalyst (130 g/h) in the form of a 45% strength aqueous solution. The reactors were heated to 40° C. It is possible to use a formaldehyde mixture having a low methanol content, as described in the German application with the title "Verfahren zur Herstellung von Polyalkoholen mit Methanol-armem Formaldehyd" [Process for the preparation of polyalcohols using formaldehyde having a low methanol content], file reference 199 63 438.6 (applicant: BASF AG).

The discharge was passed directly into the upper part of a falling-film evaporator with attached column (11 bar heating steam) and separated there by distillation under atmospheric pressure into a low-boiling top product, essentially containing n-butyraldehyde, ethylacrolein, formaldehyde, water and trimethylamine, and a high-boiling bottom product.

The top product was condensed continuously and was recycled into the reactors described above.

The high-boiling bottom product from the evaporator (about 33.5 kg/h) was continuously mixed with fresh trimethylamine catalyst (50 g/h, in the form of the 45% strength aqueous solution) and fed into a heatable tubular reactor provided with packings and having an empty volume of 12 l. The reactor was heated to 40° C.

The discharge of the downstream reactor was fed continuously into the upper part of a further distillation apparatus, for the removal of formaldehyde (11 bar heating steam) and separated there by distillation into a low-boiling top product, essentially containing ethylacrolein, formaldehyde, water and trimethylamine, and a high-boiling bottom product. The low-boiling top product (27 kg/h) was condensed continuously and was recycled into the first stirred kettle, whereas the high-boiling bottom product was collected.

The bottom product thus obtained contained essentially dimethylolbutyraldehyde, formaldehyde and traces of monomethylolbutyraldehyde in addition to water.

The following Examples1 to 4 describe the better removal of formaldehyde and the reduced formation of high boilers, which are permitted by the higher dilution according to the invention.

EXAMPLE 1

The formaldehyde is removed by distillation from the mixture of the aldol condensation of formaldehyde with n-butyraldehyde, which mixture is obtained as described above. The reaction mixture contains 9.4% of dimethylolbutanal (DMB), 11.4% of formaldehyde and water. The removal is effected in a column having a reflux ratio of 0.33. The top pressure is 1.5 bar. In the case of a feed rate of 18 kg/h, the formaldehyde content in the bottom of the column can be reduced to 3.4% by weight. This bottom product of a column is then subjected to a generally known hydrogenation. Thereafter, 8% of high-boiling acetals are present in the hydrogenated bottom product, this being understood as meaning the total of the dimethylolbutane and the trimethylolpropane acetals. There are also 4.3% of further high boilers.

EXAMPLE 2

The procedure is as described above under Example 1, but 1.5 kg/h of liquid water are added to the feed. The formaldehyde concentration in the bottom decreases to 1.79% by weight. After the hydrogenation, the acetal concentration is 4.3% and the concentration of the further high boilers is 3.2%.

EXAMPLE 3

The procedure is as described under Example 2, but 1.5 kg/h of water are additionally fed into the bottom of the column, so that altogether 3 kg/h of water are added. The formaldehyde content decreases to 0.98% by weight. After the hydrogenation, 4.7% of acetals and 4.9% of further high boilers are present in the bottom.

EXAMPLE 4

An aldol condensation product obtained as described above and containing 9.5% of DMB and about 17% by weight of formaldehyde is separated by distillation in the column described in Example 1. The top pressure is 2 bar and the reflux ratio is 0. 4.5 kg/h of steam are fed into the bottom. The feed of the aldol condensation mixture is 25.6 kg/h, and the formaldehyde content in the bottom can thus be reduced to 0.4% by weight. In the hydrogenated bottom product of the column, the acetal concentration is 1.5% and the concentration of the further high boilers is 2.8%.

In Examples 5 to 8 below, the effect of a greater dilution according to the present invention on the selectivity of the hydrogenation is demonstrated.

EXAMPLES 5 TO 8

An aldol condensation mixture which was obtained as described above is used.

The aqueous solutions thus obtained are hydrogenated at 90 bar and 120° C. in the main reactor and 130° C. in the downstream reactor by the circulation/trickle-bed procedure over a Cu/TiO$_2$ catalyst, prepared analogously to catalyst F of DE 198 09 418 and containing 47% by weight of CuO on TiO$_2$. The apparatus used consists of a 160 ml main reactor and a 50 ml downstream reactor, which are regulated by level control. The circulation rate is 1.0 l/h.

In the table below, the stated space velocity relates to the amount of organic material in the feed. The conversion and selectivity which were determined with a starting material which contained 65% of organic material or 40% of organic material are also shown, this latter solution having been obtained from the 65% strength solution by dilution with water. The selectivity relates to the amount of dimethylolbutanal used.

| Expl. | Starting material [%] | Space velocity [kg org./ 1 cat. · h] | Conversion [%] | Selectivity [%] | Yield [%] |
|---|---|---|---|---|---|
| 5 | 65 | 0.29 | 98.59 | 87.05 | 85.83 |
| 6 | 40 | 0.29 | 100.00 | 93.77 | 93.77 |
| 7 | 65 | 0.40 | 99.34 | 89.27 | 88.68 |
| 8 | 40 | 0.40 | 99.79 | 91.34 | 91.15 |

In Examples 9 and 10 below, the effect of higher dilution according to the present invention with respect to the increase in the time-on-stream or the reduction of the deactivation of hydrogenation catalyst is illustrated.

EXAMPLE 9 (Comparative Example)

The aqueous solution obtained in Example 1 is hydrogenated at 90 bar and 115° C. (main reactor temperature) by the circulation/trickle-bed procedure. The catalyst is prepared analogously to catalyst D of DE 198 09 418. It contains 24% of CuO, 20% of Cu and 46% of $TiO_2$. The apparatus used consists of a 10 ml long heated reactor of nominal diameter 25, a pressure separator and a circulation pump. The circulation throughput is 25 l/h of liquid and the reactor feed is brought to 4 kg/h.

At start-up, a DMB conversion of >99.8% is achievable. In the course of 10 weeks, during which the reactor is operated continuously, the conversion decreases to 91%.

EXAMPLE 10

The procedure is described under. Example 9, using a catalyst of the same type. However, water was metered in, as described in Example 4.

At startup, a DMB conversion of >99.8% is measured, which decreases to only 98.6% in the course of 10 weeks of continuous operation.

We claim:

1. A process for the removal, by distillation of formaldehyde from reaction solutions containing a methylolated alkanal which was obtained from the reaction of formaldehyde with an alkanal which has at least one acidic hydrogen atom α to the carbonyl function or from the reaction of a 2-alkylacrolein or acrolein with water and formaldehyde, this reaction having been carried out in the presence of catalytic amounts of an organic amine wherein the removal is effected in a distillation column and an effective amount of water in the form of steam is added before and/or during the distillation, wherein the added water is in addition to any water present or produced in the reaction of the formaldehyde with said alkanal or from the reaction of said alkylacrolein or acrolein with water and formaldehyde.

2. The process of claim 1, wherein from 0.1 to 10 parts of steam, based on feed stream, are fed in during the distillation.

3. The process of claim 1, wherein the distillation is operated at from 50 to 160° C., from 20 mbar to 5 bar, and a reflux ratio of from 100 to 0.

4. The process of 3, wherein the distillation is operated at from 1 to 3 bar.

5. The process of claim 3, wherein the distillation is operated at from 1.5 to 3 bar.

6. The process of claim 3, wherein the distillation is operated at a reflux ratio of from 3 to 0.

7. The process of claim 1, wherein the column is operated with an evaporator and the steam is fed in below the feed stream or with the feed stream.

8. The process of claim 7, wherein the steam is fed into the bottom of the column or into the evaporator.

9. The process of claim 1, wherein the number of theoretical plates of the column is from 3 to 100.

10. The process of claim 9, wherein the number of theoretical plates is from 5 to 60.

11. The process of claim 1, wherein the residence time in the column is from 1 to 300 minutes.

12. The process of claim 11, wherein the residence time is from 10 to 180 minutes.

13. The process of claim 1, wherein the bottom of the column and the bottom of the evaporator are designed in such a way that the residence times are from 1 to 300 minutes, based on the bottom discharge.

14. The process of claim 13, wherein the residence times are form 5 to 120 minutes.

15. The process as claimed in claim 1, wherein the column is operated with an evaporator having a low wall temperature and small liquid content, as used in falling-film evaporators, and a condenser with liquid recycling.

16. The process of claim 15, wherein the evaporator is a falling-film evaporator.

17. The process of claim 15, wherein the condenser is a quench.

18. A process for the preparation of polyols, wherein a methylolated alkanal which was freed from formaldehyde by the process as claimed in claim 1 is subjected to a hydrogenation known per se.

19. A process as claimed in claim 18, wherein the polyol is a triol.

20. The process of claim 7, wherein the steam is fed into the evaporator.

21. The process of claim 1, wherein the effective amount of steam added is that amount that increases the removal of formaldehyde over the same process wherein less than an effective amount of steam is added.

22. The process of claim 1, wherein the aldehyde is acetaldehyde, propionaldehyde, n-butyraldehyde or a 2-alkylacrolein.

* * * * *